(12) United States Patent
James et al.

(10) Patent No.: US 9,044,553 B2
(45) Date of Patent: Jun. 2, 2015

(54) APPARATUS FOR INJECTING A PHARMACEUTICAL WITH AUTOMATIC SYRINGE RETRACTION FOLLOWING INJECTION

(75) Inventors: Adrian Benton James, Oakland, CA (US); Brian Joseph Mason, Menlo Park, CA (US); Christine Wei Hsien McElhaney, Mountain View, CA (US)

(73) Assignee: Eli Lilly and Company, Indianapolis, IN (US)

( * ) Notice: Subject to any disclaimer, the term of this patent is extended or adjusted under 35 U.S.C. 154(b) by 158 days.

(21) Appl. No.: 13/255,304

(22) PCT Filed: Mar. 8, 2010

(86) PCT No.: PCT/US2010/026503
§ 371 (c)(1),
(2), (4) Date: Sep. 8, 2011

(87) PCT Pub. No.: WO2010/104779
PCT Pub. Date: Sep. 16, 2010

(65) Prior Publication Data
US 2012/0022466 A1  Jan. 26, 2012

Related U.S. Application Data

(60) Provisional application No. 61/159,911, filed on Mar. 13, 2009.

(51) Int. Cl.
*A61M 5/32* (2006.01)
*A61M 5/315* (2006.01)
(Continued)

(52) U.S. Cl.
CPC .............. *A61M 5/3287* (2013.01); *A61M 5/50* (2013.01); *A61M 2005/2488* (2013.01);
(Continued)

(58) Field of Classification Search
CPC ..................... A61M 5/3287; A61M 2005/206; A61M 5/2033; A61M 5/3202; A61M 2005/2488; A61M 5/326; A61M 5/3158; A61M 5/31591; A61M 5/50
USPC ......... 604/192, 198, 218, 222, 223, 242, 229, 604/228, 233
See application file for complete search history.

(56) References Cited

U.S. PATENT DOCUMENTS

| | | | |
|---|---|---|---|
| 4,957,490 | A | 9/1990 | Byrne et al. |
| 4,988,339 | A | 1/1991 | Vadher |

(Continued)

FOREIGN PATENT DOCUMENTS

| | | | |
|---|---|---|---|
| WO | 2004032989 A2 | 4/2004 | |
| WO | 2007047200 | 4/2007 | |

(Continued)

*Primary Examiner* — Theodore Stigell
*Assistant Examiner* — Lauren M Peng
(74) *Attorney, Agent, or Firm* — Edward J. Prein

(57) ABSTRACT

A pharmaceutical delivery apparatus with an automatic syringe retraction following a manually controlled injection. The apparatus includes a housing (28), a syringe carriage (90), a medication-filled syringe (70) held within the carriage, the syringe needle tip being disposed within the housing in a first position and projecting from the housing beyond the housing proximal end for insertion into an injection site in a second position, a manually shiftable plunger (130), means on the carriage and the housing and the plunger for causing the carriage to advance from the first position to the second position and for injecting medicine from the syringe when the plunger is manually plunged proximally toward the housing, and means on the carriage and the plunger for causing the carriage to retract from the second position to a position at which the needle tip is disposed within the housing when the plunger shifts distally.

6 Claims, 11 Drawing Sheets

(51) Int. Cl.
  *A61M 5/00*  (2006.01)
  *A61M 5/50*  (2006.01)
  *A61M 5/24*  (2006.01)
  *A61M 5/20*  (2006.01)

(52) U.S. Cl.
  CPC .......... *A61M 5/3158* (2013.01); *A61M 5/2033* (2013.01); *A61M 5/31591* (2013.01); *A61M 5/3202* (2013.01); *A61M 2005/206* (2013.01); *A61M 5/3204* (2013.01); *A61M 5/326* (2013.01); *A61M 2005/3247* (2013.01)

(56) References Cited

U.S. PATENT DOCUMENTS

| | | | |
|---|---|---|---|
| 5,271,744 A | 12/1993 | Kramer et al. | |
| 5,330,430 A | 7/1994 | Sullivan | |
| 5,346,480 A | 9/1994 | Hess et al. | |
| 6,210,369 B1 | 4/2001 | Wilmot et al. | |
| 6,454,743 B1 * | 9/2002 | Weber | 604/131 |
| 6,475,194 B2 | 11/2002 | Domici, Jr. et al. | |
| 6,511,460 B1 | 1/2003 | Arnissolle | |
| 6,638,256 B2 | 10/2003 | Jansen et al. | |
| 6,656,163 B1 | 12/2003 | Marshall et al. | |
| 6,692,469 B1 | 2/2004 | Weekes et al. | |
| 6,692,470 B2 | 2/2004 | Sanpietro | |
| 6,706,019 B1 | 3/2004 | Parker et al. | |
| 6,846,302 B2 | 1/2005 | Shemesh et al. | |
| 6,939,330 B1 | 9/2005 | McConnell-Montalvo et al. | |
| 6,966,898 B1 | 11/2005 | Pouget et al. | |
| 6,997,901 B2 | 2/2006 | Popovsky | |
| 7,066,907 B2 | 6/2006 | Crossman et al. | |
| 7,097,634 B2 | 8/2006 | Gilbert | |
| 7,247,151 B2 | 7/2007 | Slawson | |
| 7,297,136 B2 | 11/2007 | Wyrick | |
| 7,344,517 B2 | 3/2008 | Schiller | |
| 7,361,160 B2 | 4/2008 | Hommann et al. | |
| 2002/0032412 A1 | 3/2002 | Riemelmoser | |
| 2002/0193746 A1 | 12/2002 | Chevallier | |
| 2005/0049561 A1 | 3/2005 | Hommann et al. | |
| 2005/0165360 A1 | 7/2005 | Stamp | |
| 2005/0203466 A1 | 9/2005 | Hommann et al. | |
| 2005/0277886 A1 | 12/2005 | Hommann et al. | |
| 2006/0184132 A1 | 8/2006 | Watson | |

FOREIGN PATENT DOCUMENTS

| | | |
|---|---|---|
| WO | 2008112472 | 9/2008 |
| WO | WO 2008112472 A2 * | 9/2008 |
| WO | PCTUS2011025988 | 2/2011 |

* cited by examiner

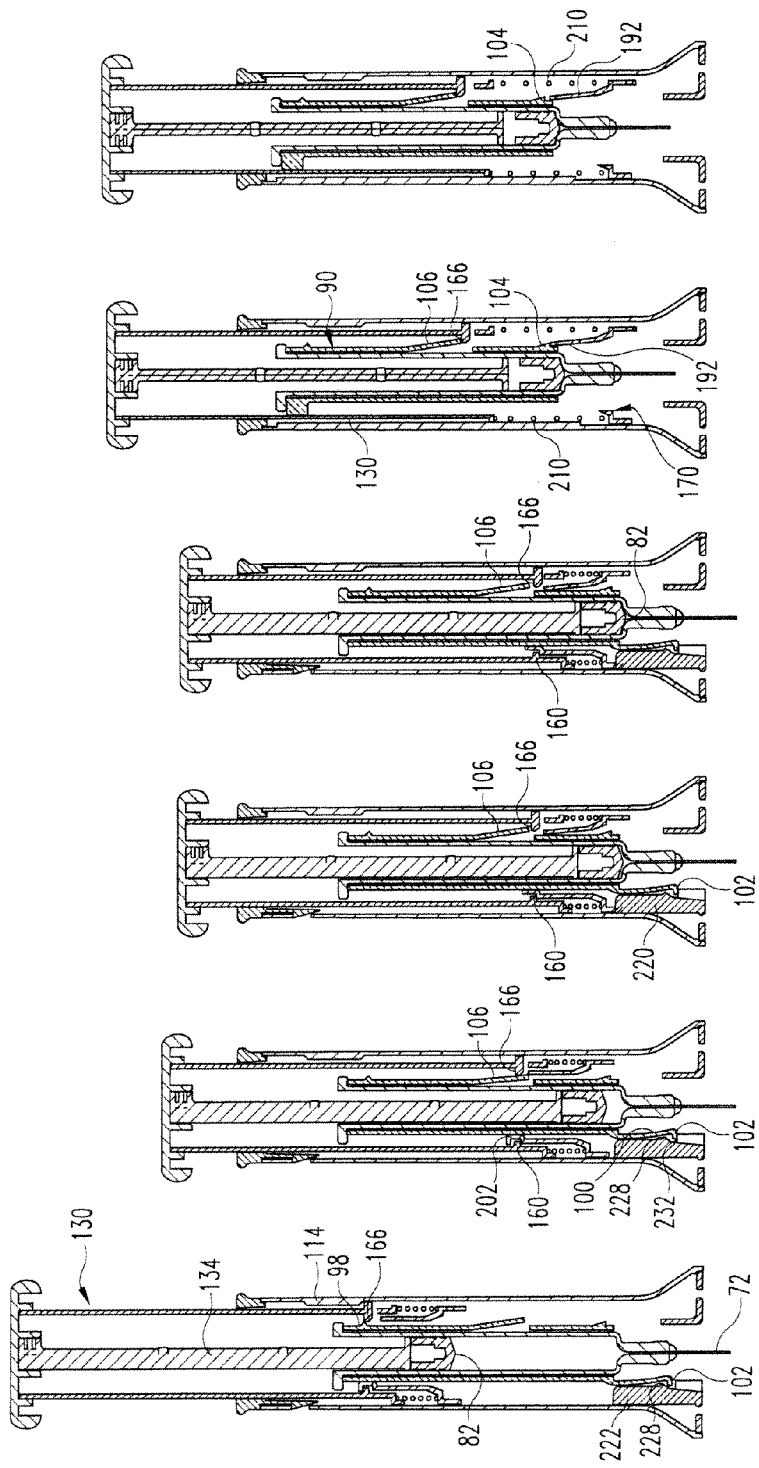

APPARATUS FOR INJECTING A PHARMACEUTICAL WITH AUTOMATIC SYRINGE RETRACTION FOLLOWING INJECTION

BACKGROUND OF THE INVENTION

The present invention pertains to pharmaceutical delivery devices, and, in particular, to a manually powered delivery device for injecting a pharmaceutical.

Patients suffering from a number of different diseases frequently must inject themselves with pharmaceuticals. As some patients find it difficult to insert a standard syringe needle into one's skin and then operate the syringe to inject the pharmaceutical, a variety of devices have been proposed to facilitate the injection process.

One type of device automatically inserts a needle and then automatically injects a dose of medication through that inserted needle. While useful, these devices may be expensive to provide due to their complexity, and further may be undesirable to users who want more control over the injection process.

A wide assortment of injection pens are also available, which pens make manual injections easier for some people. However, most such pens, which may be suited for variable dose injections, are unnecessarily complicated if needed for only a single use.

Another type of device disclosed in a WO 2007/047200 allows for a manual needle insertion and manual injection of medication in a user friendly fashion. However, this type of device provides for a manual and not an automatic needle retraction following injection into a protected position within the housing, which may not be intuitive for all users.

Thus, it would be desirable to provide a device that can overcome one or more of these and other shortcomings of the prior art.

BRIEF SUMMARY OF THE INVENTION

In one form thereof, the present invention provides a pharmaceutical delivery apparatus including a housing extending between a distal end and a proximal end, a syringe carriage rotatably fixed and axially movable within the housing between a first position and second position, a medication-filled syringe held within the carriage and including a needle having a proximal tip, the needle tip being disposed within the housing when the carriage is in the first position, the needle tip projecting from the housing beyond the proximal end for insertion into an injection site when the carriage is in the second position, a plunger axially extending from the housing distal end and manually shiftable in the proximal direction, the plunger rotatably fixed and axially movable within the housing, means on the carriage and the housing and the plunger for causing the carriage to advance from the first position to the second position and for injecting medicine from the syringe when the plunger is manually plunged proximally toward the housing, and means on the carriage and the plunger for causing the carriage to retract from the second position to a position at which the needle tip is again disposed within the housing when the plunger shifts distally. The improvement to the apparatus includes a collar within the housing, the collar including at least one cammable surface, means on the collar and the plunger for releaseably latching the collar to the plunger for travel therewith during the manual shifting of the plunger in the proximal direction that causes needle insertion and injection of medicine from the syringe, the latching means being released when the collar is rotated from a first angular orientation within the housing to a second angular orientation within the housing, a biasing means for forcing the collar and plunger apart in an axial direction when the latching means is released to force the plunger distally within the housing from the collar, and means on the housing for engaging the at least one cammable surface as the collar travels proximally with the plunger during injection to shift the collar rotationally from the first angular orientation to the second angular orientation, thereby releasing the latching means to allow the biasing means at an end of injection to drive the plunger distally and retract the needle tip by action of the means on the carriage and the plunger for causing the carriage to retract.

One advantage of the present invention is that a, single use medication delivery device may be provided which allows for a convenient manual control of medication injection, and which causes its syringe needle to be automatically retracted once the device has been used for medication administration.

Yet another advantage of the present invention is that a medication delivery device may be provided which allows its syringe needle to be automatically locked against reuse during its automatic retraction following its manually controlled medication administration.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein:

FIG. 9 is a longitudinal cross-sectional view similar to that of FIG. 8 as the delivery device is in process of having its syringe advanced during needle insertion;

FIG. 10 is a longitudinal cross-sectional view similar to that of FIG. 9 as the delivery device is in the process of having its contained medication injected through the inserted syringe needle;

FIG. 11 is a longitudinal cross-sectional view similar to that of FIG. 9 as the delivery device is near the end of its contained medication injection and at which time the retracting assembly has been shifted to an operational state;

FIG. 12 is a longitudinal cross-sectional view similar to that of FIG. 9 after the delivery device contents have been administered and before a manual plunging force has been removed from the plunger;

FIG. 13 is a longitudinal cross-sectional view similar to that of FIG. 9, but taken along line 13-13 of FIG. 1, after the manual plunging force has been removed from the plunger and during the retraction of the syringe by operation of the retracting assembly; and FIG. 14 is a longitudinal cross-sectional view similar to that of FIG. 13 of the device in a final state after the syringe has been fully retracted and locked against further use.

Figure 1:
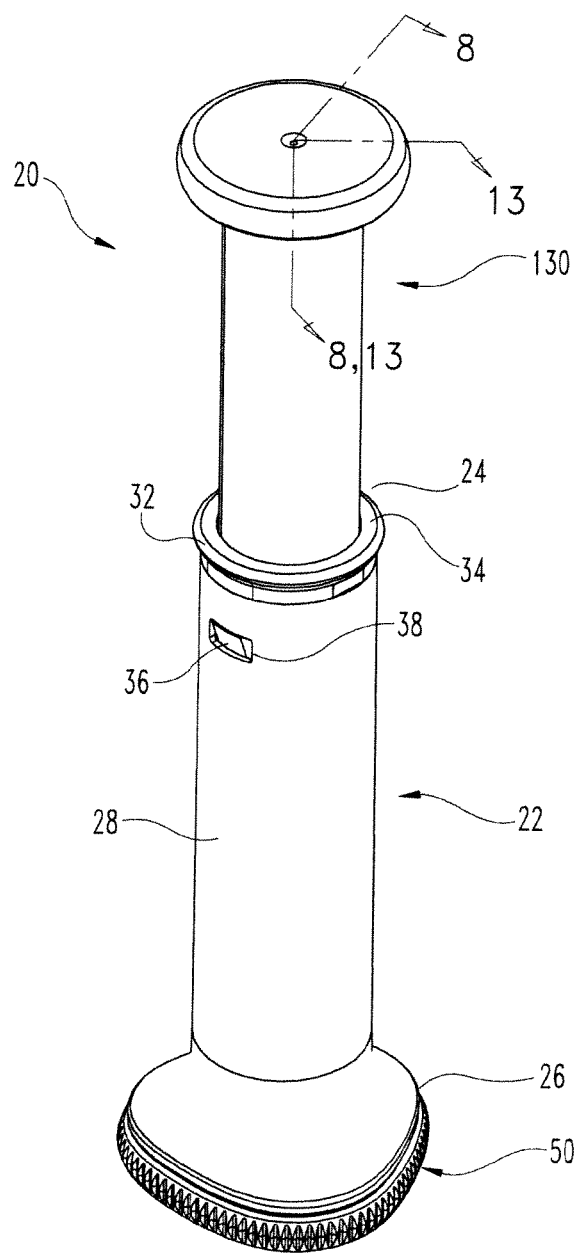
FIG. 1 is a perspective view of one embodiment of a pharmaceutical delivery device of the present invention in an initial or ready arrangement.
Figure 2:
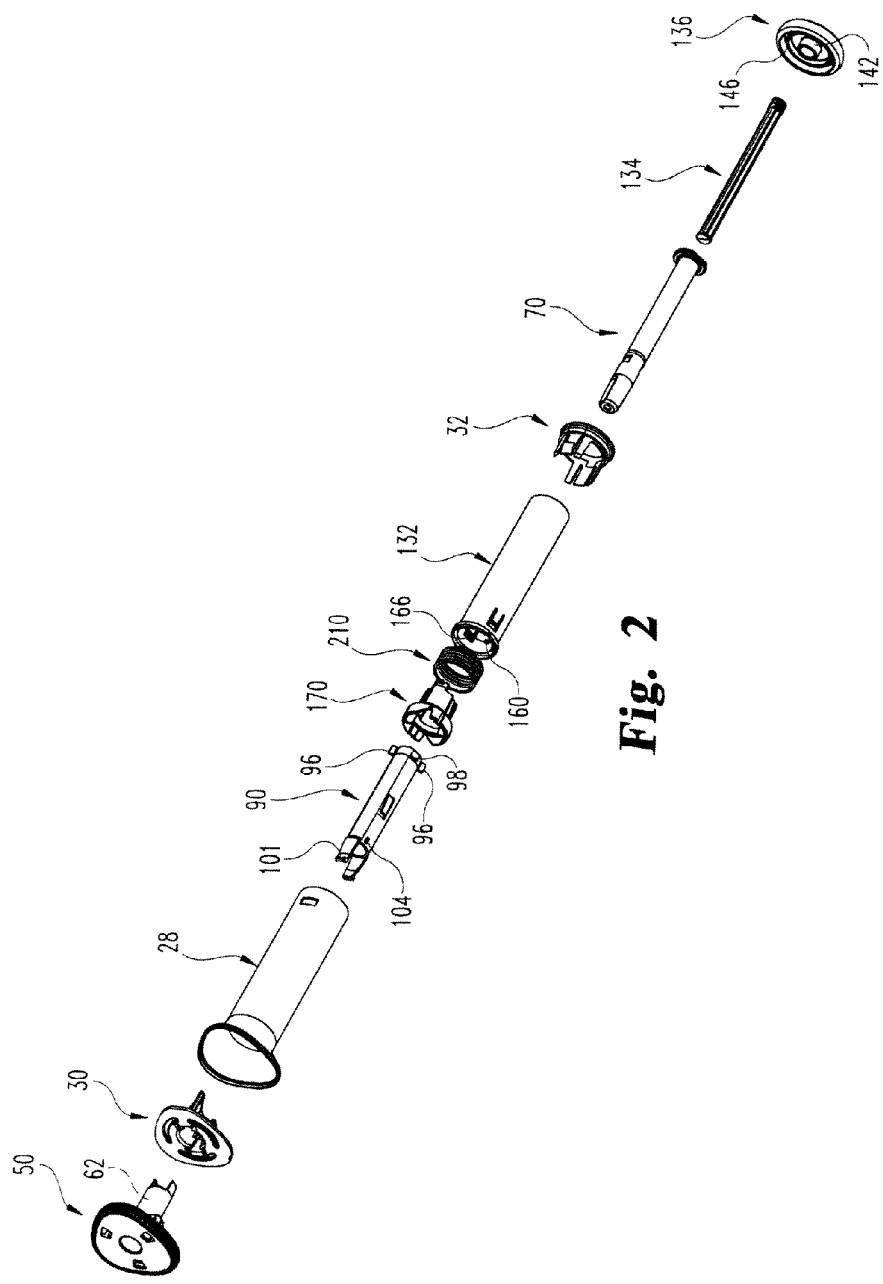
FIG. 2 is a perspective, exploded view of the pharmaceutical delivery device of FIG. 1.
Figure 3:
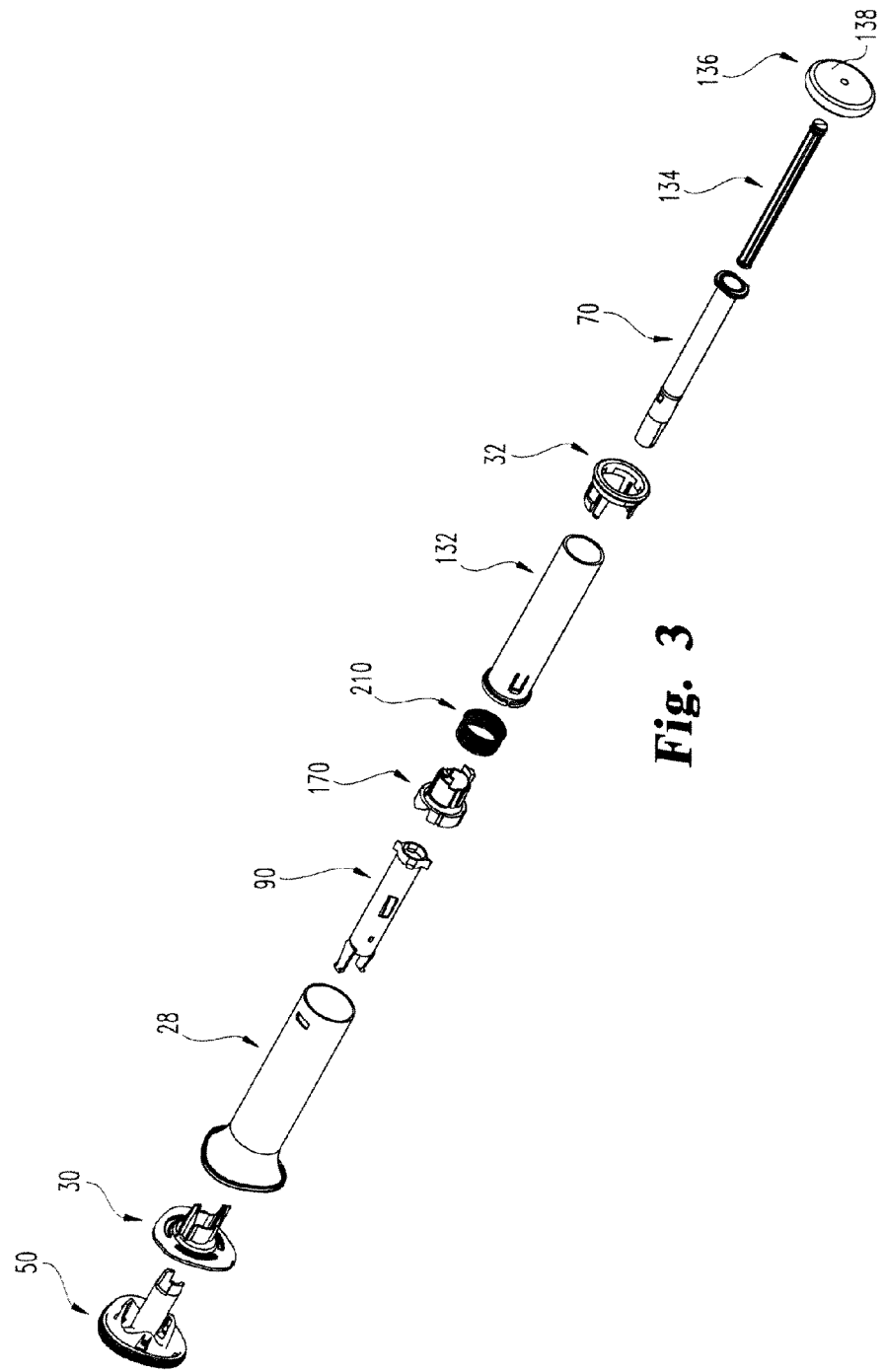
FIG. 3 is a another perspective, exploded view of the pharmaceutical delivery device of FIG. 1.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION OF THE INVENTION

Referring now to FIGS. 1-14, there is shown one embodiment of a pharmaceutical delivery device of the present invention. The delivery device, generally designated 20, is a single use delivery device. Device 20 is based on a standard, prefilled syringe as primary containment, but may be adapted for other syringes. Device 20 is delivered ready to use, and is operable to provide a single, fixed dose delivery of its prefilled medication. The device is functionally similar in many respects to those disclosed in WO2007/047200, which publication is incorporated herein by reference.

Any directional references in this detailed description with respect to the Figures, such as up or down, or top or bottom, or front and side, are intended for convenience of description, and by itself does not limit the present invention or any of its components to any particular positional or spatial orientation.

Delivery device 20 is designed to allow a user, with one hand on the device, to comfortably position the device on the skin at a pre-selected site for injection. After such siting, typically the user's other hand can be used to manually drive down the device plunger to cause needle insertion and drug delivery. When the driving plunging force is removed from the device plunger, the syringe needle automatically retracts within the device housing, and is automatically locked therein.

Delivery device 20 includes an outer housing, generally designated 22, having a distal end 24 and a proximal end 26. As used herein, distal and proximal refer to axial locations on the delivery device relative to an injection site when the device is oriented for use at such site, whereby, for example, proximal end of the housing refers to the housing end that is closest to such injection site.

The exterior periphery of outer housing 22 is sized, shaped and constructed of materials to facilitate being gripped within one hand by a user or a caregiver during site selection and injection. Outer housing 22 is shown formed by a main body 28, an end plate 30, and a body collar 32 that are fixedly attached together. Collar 32 has an annular portion 34 from which depends a pair of latching prongs 36 that snap fit through openings 38 in main body 28 during assembly to fixedly secure collar 32 with body 28. Collar 32 may be made of a suitable material, such as ABS plastic, to provide stabilization with limited resistance to the plunger as it guides its sliding motion during use. Body 28 and plate 30 may be formed of one or more materials, including clear plastics and with soft touch covering particularly on its grippable portions, and each may be assembled from more than just the single injection molded part shown.

Plate 30 includes a skin-contacting surface 40 and an upper surface 42, and is formed with a central aperture 44 for needle passage and three arcuate slots 46. A plastic needle cap 50 designed to be removed manually by a person before injection includes a base 52 with a knurled periphery, and an upstanding sleeve 54 that fits through aperture 44. Three curved cams 56 that fit within slots 46 are disposed outward of sleeve 54 and facilitate cap removal. The base of each cam 56 is also formed with an outward facing snap feature 58 that, once inserted through the slots 46, snap fits outward to releasably engage plate surface 42 to keep cap 50 in place on the device 20 until purposefully removed.

Sleeve 54 includes at its distal end a pair of diametrically opposed prongs 60. Sleeve internal hollow 62 accommodates the injection needle 72 of the syringe 70, as well as elastomeric sealing shield 74 and rigid cover 76 that effectively serve as part of the cap. When cap 50 is removed from the configuration shown in FIG. 1, latching hooks on prongs 60 engage the distal surface of rigid cover 76 and serve to remove the shield 74 and cover 76 from the needle 72 to expose the needle tip within the housing for subsequent use.

Syringe 70 is of suitable known design and includes barrel 80 to which needle 72 is mounted, and an elastomeric stopper or piston 82 that slidably seals the distal end of the medicine filled interior 84.

A syringe carriage 90 of device 20 is disposed within outer housing 22. Carriage 90 is rotatably fixed relative to outer housing 22 such as further described below, but is selectively axially movable therein to allow for device functionality. Carriage 90 is formed in one piece from a suitable plastic material and includes a tubular body 92 having a distal end 94 which serves as a seat upon which fits the flange 86 of the syringe barrel 80 which projects at its distal end. Syringe barrel 80 fits within an interior hollow 93 of body 92, and a pair of not shown, longitudinally extending ribs that are formed on the carriage body interior surface that defines hollow 93 provide a friction fit that keeps the syringe 80 in a rotationally and axially fixed orientation relative to the carriage 90. Other substitutable or additional securing means, such as a clip at the top of the carriage, may be used to keep the cartridge and syringe together.

At its distal end, tubular body 92 includes a pair of guide keys or wings 96 that are integrally formed with and project radially outward from the outer periphery of body 92. Staging nubs 98 are disposed on the carriage body periphery between keys 96. Nubs 98 are integrally formed with and project radially outward from body 92 a distance less than keys 96. Nubs 98 serve as push surfaces against which an axial force can be applied by the plunger to carriage 90 to drive the carriage and held syringe proximally to cause needle insertion.

Projecting from its proximal end, carriage body 92 includes a pair of axially extending, flexible legs 100 that are diametrically disposed. A detent 102 is formed on the outer region of each leg 100 at its proximal end. The inner face of each proximal leg end includes a slight beveling or ramping that cooperates with a beveled edge of cap sleeve 54 to bend legs 100 outward during assembly.

Carriage body 92 includes a pair of nubs 104 formed on its exterior at a one hundred eighty degree angular spacing and near the proximal end of body 92. Nubs 104 project radially outward and serve as retraction lock features that cooperate with complementary features of the biasing member retaining collar to lock the syringe in a retracted position within the housing after the syringe has been retracted automatically following use.

Carriage body 92 also includes a single resilient capture or latching tang 106 disposed distally of and angularly offset from latching nubs 104. Tang 106 projects at an angle from body 92 in a direction downward and radially outward therefrom. Tang 106, due to its resilient construction, is able to bend inward and then snap back outward into a locking arrangement during passage of a plunger element during the injection process.

Figure 4:
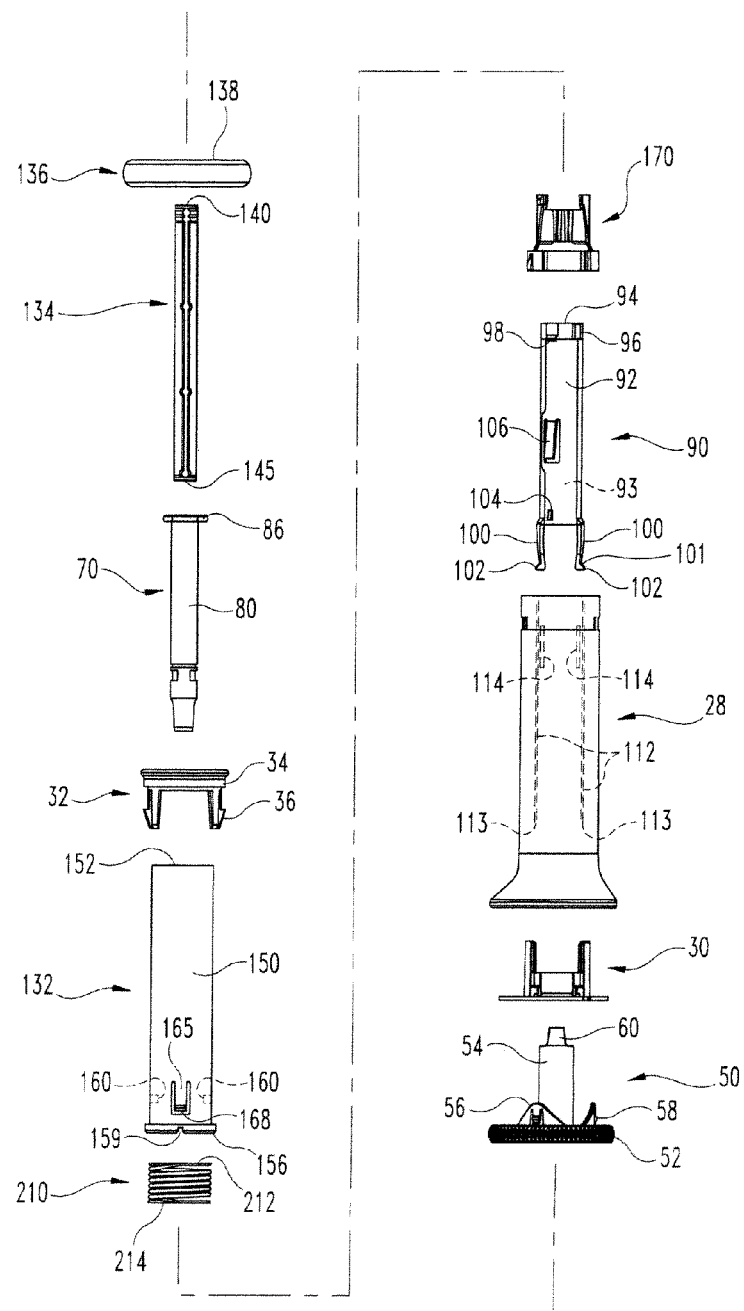
FIG. 4 is a front exploded view of the device of FIG. 1.
Figure 5:
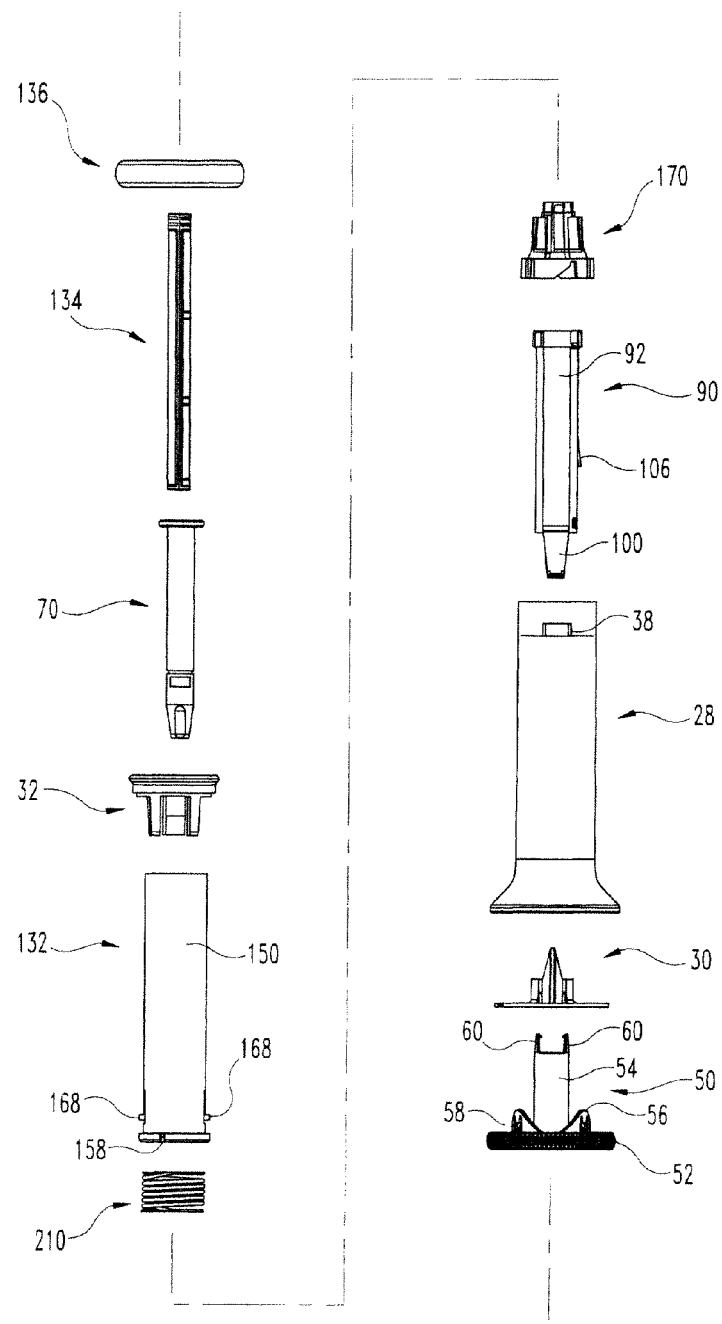
FIG. 5 is a side exploded view of the device of FIG. 1.
Figure 6A:
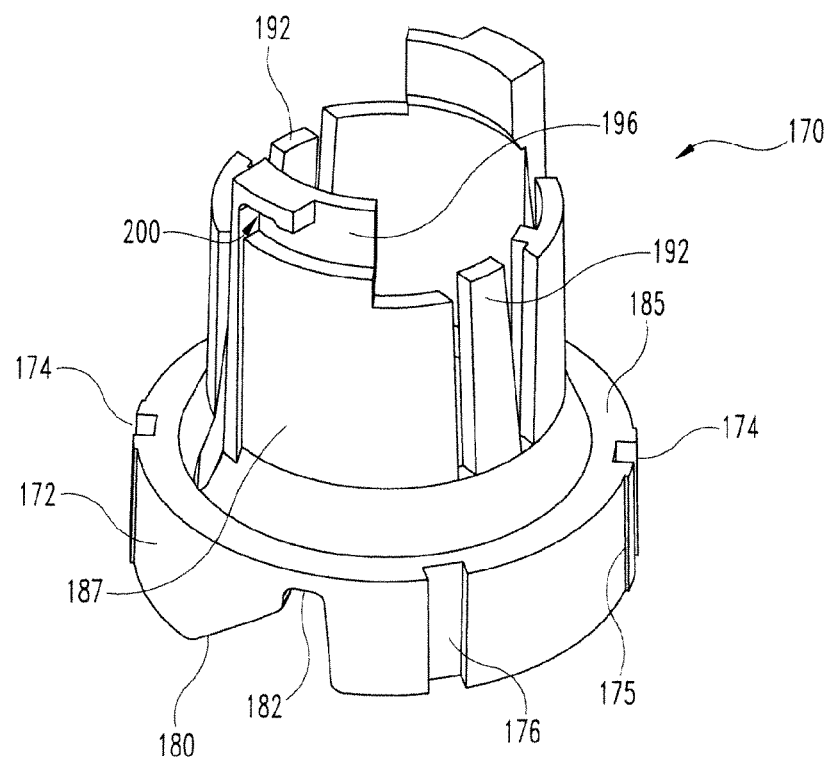
FIGS. 6A, 6B, 6C, 6D, 6E and 6F are respectively top perspective, bottom perspective, side, front, top and bottom views of the biasing member retaining collar of the device of FIG. 1.
Figure 6B:
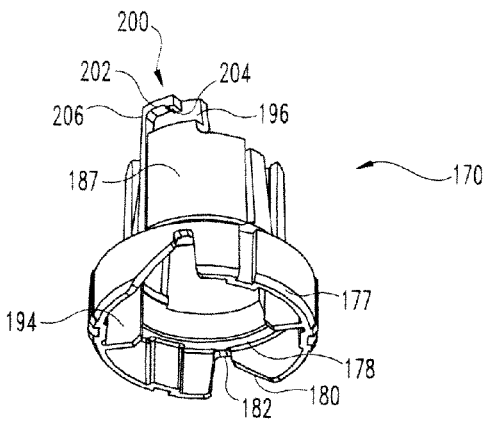
Figure 6C:
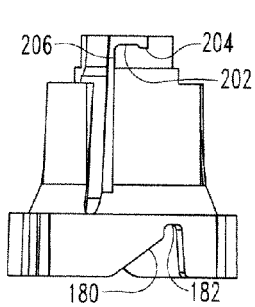
Figure 6D:
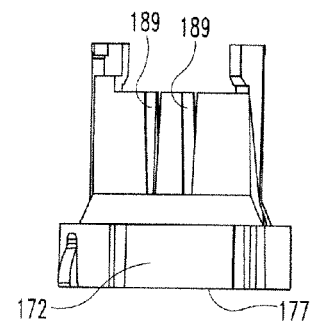
Figure 6E:
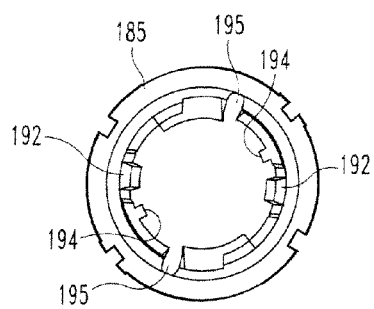
Figure 6F:
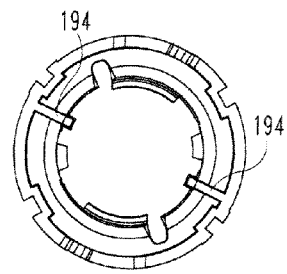
Figure 7A:
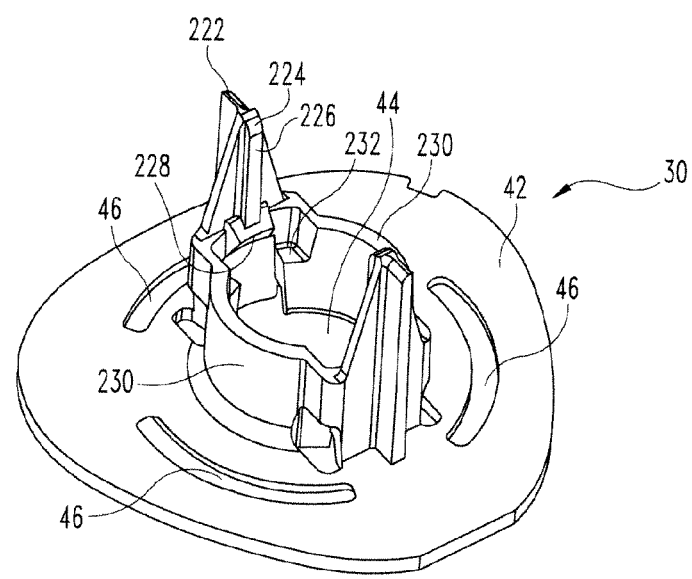
FIGS. 7A, 7B, 7C and 7D are respectively top perspective, front, side and cross-sectional views of the housing base plate of the device of FIG. 1.
Figure 7B:
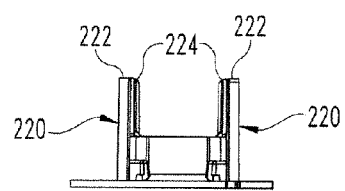
Figure 7C:
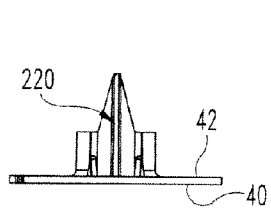
Figure 7D:
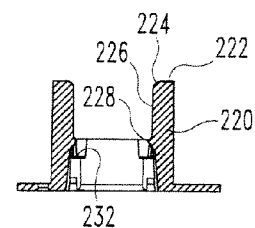

Housing body 28 includes an interior hollow 110 defined by a surface that includes a pair of diametrically opposed, longitudinally extending ribs shown in dashed lines at 112 in FIG. 4. Ribs 112 serve as keys that guide the longitudinal motion of the plunger assembly. The proximal ends of ribs 112 are indicated at 113. Angularly spaced from ribs 112 is a pair of diametrically opposed staging ribs 114 that cooperate with the plunger assembly. Each rib 114 includes a bar-shaped main section 115, a sloping surface or ramp 118 leading to the distal end of section 115, and ramp 120 at the proximal end of section 115. Ramps 118 provides a short and smooth storage of energy prior to syringe movement, and ramps 120 in effect cause the release of the carriage from direct advancement by the plunger. The ramps 118 and 120 may be of slopes selected by the designer to achieve the proper feel and operation of the pen. Suitable slopes include about forty-five degrees, and a larger slope for ramp 120 may be desirable to provide a more precise release of the plunger that defines a moment of unstaging for the shown apparatus.

The plunger of device 20 is generally designated 130 and is manually operable by a user to affect operation of the device. Plunger 130 is shown formed from plastic molded parts including a plunger sleeve 132, a plunger rod or stem 134, and a plunger cap 136 all rigidly interconnected during manufacturing assembly. Plunger sleeve 132 is disposed around and concentrically with stem 134 in a radially spaced apart relationship to define an annular gap in which freely fits portions of the carriage and syringe. The distal surface 138 of cap 136 is intended as the surface to be directly pressed on by a user to plunge the plunger. Plunger stem 134 includes a distal end 140 that is press fit, and then further secured thereat with a UV-cured adhesive, within an annular lip 142 of the proximal surface of cap 136. The plunger stem and cap may be differently attached, such as via a snap fit. The proximal end 145 of plunger stem 134 is sized to fit freely within syringe barrel 80 for a direct pushing engagement of syringe piston 82.

Plunger sleeve 132 has a cylindrical tubular body 150 including a distal end 152 that is press fit, and then further secured thereat with a UV-cured adhesive, within a second annular lip 146 of cap 136. The plunger sleeve and cap may be differently attached, such as via a snap fit. A circumferential, beveled shoulder or lip 156 extends around the proximal end of sleeve 132. A first pair of diametrically opposed and longitudinally extending slots or notches 158 in lip 156 accommodate housing ribs 112 and serve as guide slots whereby rotational motion of the plunger sleeve 132 relative to the housing 28 is prevented at all times throughout the plunger travel as it moves longitudinally within the housing during use. A second pair of diametrically opposed, longitudinal slots 159 in lip 156 that are angularly spaced from lip slots 158 serve as clearance slots allowing for passage of staging ribs 114. Lip 156 prevents improper withdrawal of the plunger from the housing by the user prior to injection by an interference with body collar 32.

The interior surface of plunger sleeve 132 is provided with a pair of longitudinally extending guide grooves that are not shown. The guide grooves slidably receive carriage keys 96 to effectively rotatably lock the carriage 90 and plunger element 130 together at all times while allowing relative axial motion as further described below. As shown in dashed lines at 160 in FIG. 4, the interior surface of plunger sleeve 132 also includes a pair of nubs that are diametrically opposed. Nubs 160 serve as latching features that cooperate with complementary features of the biasing member retaining collar to releasable latch together the biasing member retaining collar described below and the carriage 90 during manufacturing assembly.

A pair of diametrically opposed resilient prongs 165 are formed in plunger sleeve 132 near its proximal end. Each of prongs 165 includes at its proximal end an inwardly projecting tab 166 seen in FIG. 2, and a radially outwardly projecting tab 168. Tabs 166 are structured to drivingly engage carriage staging nubs 98 when the prongs 165 are bent inward when tabs 168 slide along housing ribs 114 during the plunging of plunger 130 relative to the housing 22 from the ready position shown in FIG. 1.

The automatic syringe retraction feature of device 20 uses a biasing member retaining collar, generally designated 170, that is further shown in FIGS. 6A-6F. Collar 170 fits freely around the carriage 90 concentrically therewith so as to be moveable axially and rotatably relative to the carriage until it lockingly engages the carriage after syringe retraction following injection. Biasing member retaining collar 170 includes a ring-shaped body 172 that extends completely around carriage 90 when device 20 is assembled. Collar body 172 includes a pair of longitudinally extending notches 174 formed in its outer periphery which accommodate housing ribs 112. Small longitudinal ribs 175 shown flanking each of notches 174 are provided for tolerance control. Collar body 172 includes a second pair of longitudinally extending notches 176 that are angularly spaced from notches 174 around the outer periphery and serve as clearance slots allowing for passage of staging ribs 114. A pair of notches each including ramp surface 180 and an enlarged seating surface 182 are formed in the lower face 177 of body 172 at a one-hundred and eighty degree interval. Within the interior of collar 170, a generally annular, proximal facing surface 178 of body 172 serves as a physical stop for abutment by the flats 101 on the distal faces of the carriage detents 102 during syringe retraction.

The upper face 185 of body 172 transitions to an upstanding tube portion 187 that is interrupted along its circumference by opposing pairs of open ended slots 189 that define resilient locking tangs 192 that flex outward and then snap inward as described below to perform a carriage locking. Diametrically opposed notches 195 in tube portion 187 are provided to allow passage of carriage guide keys 96 during manufacturing assembly. Two axially oriented ribs 194 protrude from the interior surface of collar 170 along its axial height. Ribs 194 serve to maintain a centering of the device components. Along the distal edge of tube portion, a pair of plunger latching features is formed spaced apart at a one hundred eighty degree interval. Two latching features are preferred to balance forces, but different numbers of such features, including as few as a single such feature, may be employed. Each latching feature includes a lip, generally designated 200, which projects radially outward of so as to overhang an inwardly recessed region 196 of tube portion 187. Lip 200 includes a retaining segment 202 that extends in a circumferential direction, as well as a short catch segment 204 and an end wall segment 206 that depend from retaining segment 202. Lip 200 is sized and configured with the plunger nub 160 so as to fit thereover, with the nub 160 in contact with lip 200, and more particularly the proximal surface of retaining segment 202, and with the nub projecting toward recessed region 196 within the space axially below lip segment 202 and angularly between the wall segment 206 and catch segment 204. In such an arrangement, the collar 170 is releaseably latched with the plunger. Recessed region 196 provides extra space in the shown embodiment to fit nub 160 and allow for more material in the radial direction and therefore more robust lip engagement. In addition, the wall defining the back of recessed region 196, by virtue of its proximity to the outer surface of carriage body 92, prevents lip 200 from flexing radially inwardly during device storage or operation. Wall segment 206 serves to add rigidity to lip 200, and catch segment 204 provides a detenting feature for the nub which is useful to maintain component alignment during manufacturing assembly.

A biasing member acting to force plunger 130 and collar 170 apart is part of the automatic syringe retraction feature of device 20. In the shown embodiment, the biasing member is in the form of a preloaded element captured between the plunger and collar. The biasing member is a coiled metal compression spring 210 that fits around collar tube portion 187. The distal end 212 of spring 210 abuts the underside of plunger sleeve lip 156 and the proximal end 214 of spring 210 abuts the upper face 185 of collar body 172.

Figure 8:
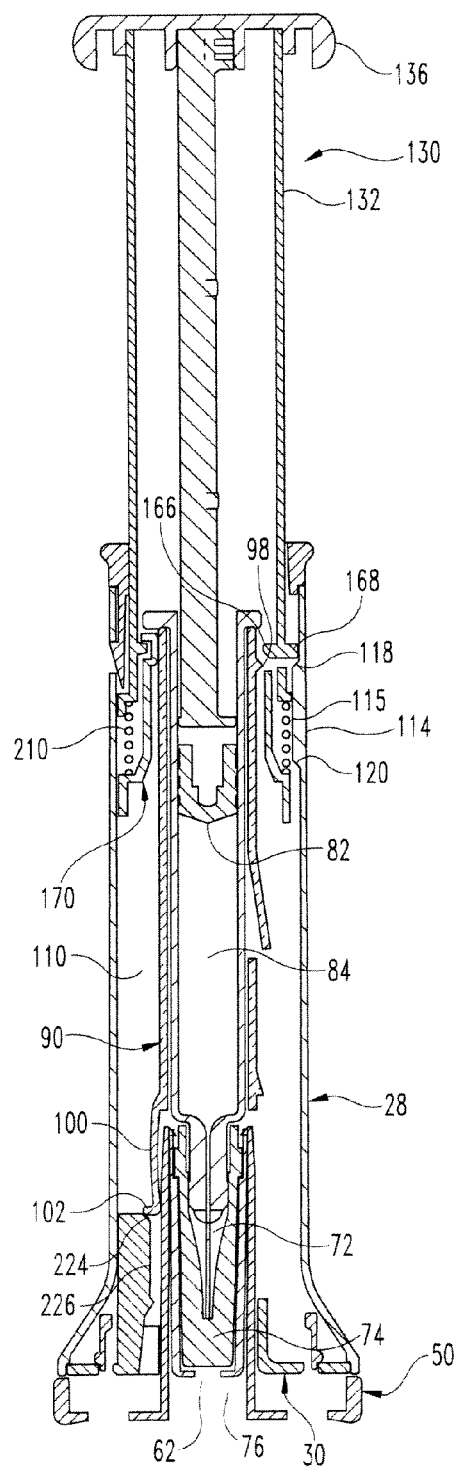
FIG. 8 is a longitudinal cross-sectional view of the delivery device, taken along line 8-8 of FIG. 1.

When plunger 130 and collar 170 are latched together when device 20 is in a ready state such as shown in FIGS. 1 and 8, which latching results form the engagement of collar lips 200 and plunger nubs 160, spring 210 is captured in a compressed state, and collar 170 and therefore captured spring 210 are carried with the plunger to move identically thereto. When plunger 130 and collar 170 are rotated relative to one another so as to release the latching feature and unlatch these components as further described below, the retracting assembly is operational and spring 210 tends to expand to force the plunger 130 and collar 170 axially apart. Spring 210 is selected by the designer to provide enough force to overcome the detenting force keeping the syringe carriage with the housing end plate and then to properly retract the carriage and held syringe automatically when the user removes her hand from the plunger, or otherwise stops applying any force to the plunger, at the end of injection. The spring force is less than a normal plunging force expected to be applied by a user so as to not cause the plunger to move distally unexpectedly as the user continues to plunge it until injection is complete. One suitable spring 210 applies a maximum returning force on the plunger of about 1.1 pounds.

The syringe retraction feature also uses an unlatching element axially and rotatably fixed in the housing which engages collar 170 so as to rotate the collar 170 out of latching engagement with the plunger 130. In the shown embodiment, the unlatching element is provided in the form of a pair of upstanding tabs 220 formed integrally with end plate 30. In alternate embodiment, the function of the tabs may be differently provided for, such as by ears that fixedly project inward from the interior surface of housing body 28 for engagement with the collar. Tabs 220 include radially oriented top surfaces 222 that are slidably engaged by collar ramp surfaces 180 and that fit against collar seating surfaces 182. The abutment of tab surfaces 222 by the ends of carriage legs 100 when the legs are bent outward by cap sleeve 54 frustrates the proximal plunger motion of an injection attempt prior to cap removal. The inward edge 224 of each top surface 222 is beveled to lead to a tab side surface 226 that is provided with a detent ramp 228 designed to releasable engage carriage leg detents 102. Two support members 230 that are formed integrally with the end plate extend between tabs 220 and which ring aperture 38 provide rigidity to tabs 220. Ledges 232 formed on support members 230 flank detent ramp 228 and serve as a stop surface against which abut carriage leg detents 102 to halt carriage advancement. Ledges 232 do not extend below ramp 228 to facilitate ramp molding. The height of tabs 220 is selected during design to unlatch the collar 170 from the plunger 130, thereby permitting the needle retraction once the plunger driving force is removed, at a point which guarantees that the entire desired contents of the syringe, within tolerance restrictions, have been delivered. At such point, typically the syringe piston is slightly spaced from the bottom of the syringe barrel, and the force and momentum of normal manual plunging action is believed to cause users to typically bottom out the syringe piston travel before force is removed from the plunger that allows the automatic retraction feature to cause the plunger to travel distally The collar and the device components which are physically engaged by the collar are made of materials chosen to account for the sliding motion therebetween. For example, in the shown embodiment, collar 32 is formed in one piece out of a low friction material, such as an ABS plastic molded with a lubricating additive, and the plunger sleeve 130 and end plate 30 are molded from one or more complementary plastics such as a clear ABS.

The construction of device 20 will be further understood in view of the following explanation of an exemplary operation. The user will typically be provided with a device in its capped, ready state as shown in FIGS. 1 and 8. After the user removes the cap 50 and therefore the held shield 74 and cover 76, which removal leaves the injection needle 72 uncovered but entirely within the confines of body 28, the device is manually placed with end plate 30 against the injection site. When a user then manually applies a plunging force directly on plunger cap 136, plunger 130 starts to move proximally, causing tabs 166 to abut nubs 98 due to the inward motion of the prongs 165 resulting from the sliding engagement of tabs 168 with housing ribs 114. A further manual plunging of plunger 130 starts to drive carriage 90 and its held syringe 70, as well as carries collar 170 and the captured spring 210, simultaneously, and in an equal amount, proximally as carriage legs 100 bend inward as detents 102 slide over edges 224 and along tab surface 226. As the manual plunging continues, causing the tip of injection needle 72 to pass through aperture 44 and into the user at the injection site, the carriage 90 continues to move proximally until detents 102 snap over detent ramp 228, providing an audible and tactile indication of needle insertion, at which time the plunger prongs 165 resiliently splay out of engagement with nubs 98 due to tabs 168 reaching the proximal end of ribs 114. At this point, carriage advancement due to direct engagement by the plunger sleeve has been halted and the syringe needle is effectively inserted for an injection, and the device is configured as shown in FIG. 9.

As a user continues to manually plunge the plunger 130 proximally, piston 82 is forced by plunger rod 134 to move proximally within the axially stationary syringe, forcing the medicine contained with the syringe out through injection needle 72. During this piston motion, a very small, such as about 0.5 mm, additional carriage and syringe advancement in the proximal direction relative to the housing is typical due to frictional and/or hydraulic forces, which small advancement is physically halted by the carriage leg detents 102 abutting housing plate ledges 232. FIG. 10 shows device 20 during medication injection at a point before plunger sleeve tab 166 begins camming radially inward carriage tang 106. Collar 170 remains latched with plunger element 130 by the engagement of lip segments 202 with nubs 160, only one of which is visible in FIG. 10 due to the cut line used in the view. Collar 170 is also still in a rotationally fixed arrangement with the housing 22 as its guide notches 174 still fit over housing ribs 112. Collar 170 has yet to reach a point at which it engages end plate tabs 220. FIG. 11 shows device 20 during medication injection at a subsequent point after plunger sleeve tab 166 has passed proximally the tang 106, which tang has resiliently returned to its outward extending arrangement. During the plunger movement from its position in FIG. 10 to FIG. 11, collar 170 has been carried axially therewith such that notches 174 pass the ends 113 of ribs 112, freeing one restraint against the collar rotating in the housing. In addition, collar 170 has been forcibly rotated from a first angular orientation within the housing due to its cam engagement with the plate tabs 220, so as to unlatch collar 170 from the plunger 130 to enable the retracting assembly to function. More specifically, as collar 170 has been so moved downward, ramp surfaces 180 contact tab top surfaces 222, and collar 170 is rotated as collar surfaces 180 slide along surfaces tab 222 at which the collar seating surfaces 182 reach and seat on tab top surfaces 222 that serve as physical stops to further proximal motion of the collar. At this time, in which collar 170 is at a second angular orientation within the housing where the collar lip segments 202 and catch segments 204 have been rotated over and completely clear of plunger nubs 160 so as to unlatch the collar and the sleeve thereby freeing the retraction spring 210 to act therebetween, the immediate expansion of which spring is prevented by the continued force being applied by the user to the plunger. This unlatching occurs just slightly before, as a function of the mechanical tolerance stack as previously described, the plunger 130 has reached the end of its stroke, shown in FIG. 12, at which the piston 82 has bottomed out within the syringe barrel 80 and halts all further ability of plunger 130 to be advanced proximally by the user, which bottoming out indicates to the user that injection is complete. Spring 210 is chosen to have sufficient clearance within its coils to allow for the small compression associated with this last bit of proximal movement the plunger sleeve 130 has relative to collar 170.

When a user, now aware that injection is complete, then stops applying a proximal force to plunger 130, the retracting assembly serves to retract the syringe needle within the housing automatically without further user input. Specifically, as spring 210 expands it drives plunger 130 distally relative to the housing, during which motion plunger tab 166 abuts carriage tang 106, causing carriage 90 and its held syringe 70 to be shifted distally within housing 28 with the plunger. As carriage 90 and syringe 70 are pulled upward by plunger 130, carriage nubs 104 pass collar tangs 192, which tangs bend outward resiliently when in contact with nubs 104 and which tangs then snap radially inward to a locking arrangement positioned proximally of the nubs 104. The collar 170 is prevented from being pulled upward due to the interference of housing rib ends 113 with the upper face 185 of collar body 172. At this point device 20 is arranged as shown in FIG. 13, in which arrangement syringe 70 and its needle 72 are protectively locked from proximal motion within the housing in that a direct physical abutment of the syringe carriage nubs 104 with the collar tangs 192 prevents proximal plunging of the syringe needle from the housing. Spring 210 continues to further retract the plunger and the captured carriage and held syringe into housing until the flats 101 of the carriage legs abut and are physically stopped by the collar, distal motion of which collar is prevented by rib ends 113, at which time device 20 is configured as shown in FIG. 14 ready to be disposed of properly by the user.

While this invention has been shown and described as having preferred designs, the present invention may be modified within the spirit and scope of this disclosure. This application is therefore intended to cover any variations, uses or adaptations of the invention using its general principles. Further, this application is intended to cover such departures from the present disclosure as come within known or customary practice in the art to which this invention pertains.

We claim:

1. A pharmaceutical delivery apparatus comprising a housing extending between a distal end and a proximal end, a syringe carriage rotatably fixed and axially movable within said housing between a first position and second position, a medication-filled syringe held within said carriage and including a needle having a proximal tip, said needle tip being disposed within said housing when said carriage is in said first position, said needle tip projecting from said housing beyond said proximal end for insertion into an injection site when said carriage is in said second position, a plunger axially extending from said housing distal end and manually shiftable in the proximal direction, said plunger rotatably fixed and axially movable within said housing, means on said carriage and said housing and said plunger for causing said carriage to advance from said first position to said second position and for injecting medicine from said syringe when the plunger is manually plunged proximally toward said housing, and means on said carriage and said plunger for causing said carriage to retract from said second position to a position at which said needle tip is again disposed within said housing when the plunger shifts distally, wherein the improvement comprises:

a collar within said housing, said collar including at least one cammable surface;

means on said collar and said plunger for releaseably latching said collar to said plunger for travel therewith during the manual shifting of the plunger in the proximal direction that causes needle insertion and injection of medicine from said syringe, said latching means being released when said collar is rotated from a first angular orientation within the housing to a second angular orientation within the housing;

a biasing means for forcing said collar and plunger apart in an axial direction when said latching means is released to force said plunger distally within said housing from said collar;

means axially and rotatably fixed in said housing for engaging said at least one cammable surface as said collar travels proximally with the plunger during injection to shift said collar rotationally from said first angular orientation to said second angular orientation, thereby releasing said latching means to allow said biasing means at an end of injection to drive said plunger distally and retract the needle tip by action of said means on said carriage and said plunger for causing said carriage to retract.

2. The pharmaceutical delivery apparatus of claim 1 further comprising guide means on said housing and said collar for maintaining said collar in said first angular orientation during an initial part of plunger proximal travel and for allowing rotation of said collar during a later part of plunger proximal travel, and wherein said guide means, when said collar is disposed in said second angular orientation, limits distal movement of said collar within said housing.

3. The pharmaceutical delivery apparatus of claim 1 wherein said collar comprises means for locking said carriage after retraction to prevent proximal plunging of the syringe needle from the housing.

4. The pharmaceutical delivery apparatus of claim 3 wherein said locking means comprises at least one resilient tab for sliding over and then engaging a radial projection on said carriage.

5. The pharmaceutical delivery apparatus of claim 1 wherein said biasing means comprises a compression spring captured between said collar and said plunger with a distal end abutting said plunger and a proximal end abutting said collar.

6. The pharmaceutical delivery apparatus of claim 1 wherein said at least one cammable surface comprises ramp surfaces formed by notches in a proximal face of said collar.

* * * * *